United States Patent [19]

Schmailzl et al.

[11] Patent Number: 5,107,043
[45] Date of Patent: Apr. 21, 1992

[54] PROCESS FOR THE PREPARATION A BIS(3,3-BIS(4-HYDROXYALKYLPHENYL)-BUTANOIC ACID)DIOL ESTER

[75] Inventors: Georg Schmailzl; Josef Wiedemann, both of Gersthofen; Gerhard Pfahler, Augsburg; Günther Nowy, Aystetten, all of Fed. Rep. of Germany

[73] Assignee: Hoechst Aktiengesellschaft, Frankfurt am Main, Fed. Rep. of Germany

[21] Appl. No.: 606,700

[22] Filed: Oct. 31, 1990

[30] Foreign Application Priority Data

Dec. 8, 1989 [DE] Fed. Rep. of Germany ....... 3940572

[51] Int. Cl.$^5$ .............................................. C07C 69/76
[52] U.S. Cl. ..................................................... 560/57
[58] Field of Search ........................................... 560/17

[56] References Cited

U.S. PATENT DOCUMENTS 3,450,746  6/1969  Stapfer .................................. 560/57
4,052,364  10/1977  Christidis ............................. 560/57

Primary Examiner—Paul J. Killos

[57] ABSTRACT

By dividing the known condensation of acetoacetic acid diol esters with phenols into two process steps, a reduction in the cost of the entire process can be achieved.

Methyl acetoacetate is first condensed with a phenol and the methyl 3,3-bis(4-hydroxyalkylphenyl)butanoate formed is reacted with the desired diol in the presence of a transesterification catalyst. In this way only one acetoacetic ester is necessary for various final products. The final products are useful stabilizers for plastics, in particular polyolefins.

2 Claims, No Drawings

PROCESS FOR THE PREPARATION A BIS(3,3-BIS(4-HYDROXYALKYLPHENYL)-BUTANOIC ACID)DIOL ESTER

The present invention relates to a process for the preparation of a bis[3,3-bis(4-hydroxyalkylphenyl)-butanoic acid]diol ester by condensation of an acetoacetic ester with a phenol and reaction of the condensation product with an alcohol.

Bis[3,3-bis(4-hydroxyalkylphenyl)butanoic acid]diol esters are important stabilizers for plastics, in particular for polyolefins. They are prepared by condensation of phenols of the formula

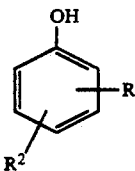

with acetoacetic esters of the formula

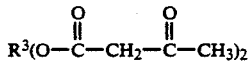

at a temperature of $-10°$ to $+15°$ C. in the presence of gaseous hydrogen chloride and a $C_8$–$C_{20}$-alkylmercaptan (cf. U.S. Pat. No. 4,022,819). Acetoacetic esters of diols are employed as starting materials and the reaction products are recrystallized from aromatic solvents. A different acetoacetic ester must be employed for each final product.

The aim existed of finding a process which is simpler to carry out and gives a comparable yield.

It has been found that this aim can be achieved if the process is carried out in two steps, methyl acetoacetate being used in the first step and being transesterified in the second step with the intended diol.

The invention thus relates to a process for the preparation of a bis[3,3-bis(4-hydroxyalkylphenyl)butanoic acid]diol ester by reaction of an acetoacetic ester with a phenol in the presence of gaseous hydrogen chloride and a $C_8$–$C_{20}$-n-alkylmercaptan, which comprises first reacting methyl acetoacetate with a phenol of the formula I

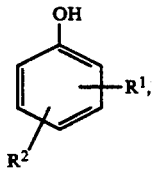

in which $R^1$ and $R^2$ are identical or different and are a hydrogen atom or an alkyl radical having 1 to 4 carbon atoms, at a temperature of $-10°$ to $+15°$ C. in the presence of 5 to 30% by weight, relative to the ester, of an n-alkylmercaptan having 8 to 20 carbon atoms and converting the resulting methyl 3,3-bis(4-hydroxyalkylphenyl)butanoate by transesterification with a diol in the presence of 0.05 to 2 mol-%, relative to the ester, of an organometallic compound of the formula II $$M(OR^3)_4 \quad (II),$$

in which $R^3$ is an alkyl radical having 1 to 18 carbon atoms, phenyl or benzyl and M is a metal of the groups IVA and IVB of the periodic table, or a dialkyltin compound of the formula III $$R_2^4 SnO \quad (III),$$

in which $R^4$ is an alkyl radical having 4 to 12 carbon atoms, at a temperature of 120° to 240° C. and a pressure of 2 to 300 mbar into the bis[3,3-bis(4-hydroxyalkylphenyl)butanoic acid]diol ester, which is freed from all distillable components by distillation at a temperature of 220° to 280° C. and a pressure of 0.2 to 8 mbar.

Methyl acetoacetate is employed as a starting material for the process according to the invention. This ester can be prepared by addition of diketene to methanol in the presence of a basic compound, for example triethylamine, as a catalyst.

The ester is reacted with a phenol in the first step.

Suitable phenols are principally those phenols which are unsubstituted in the 4-position, of the formula I

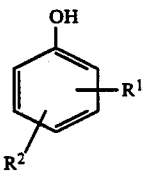

in which $R^1$ and $R^2$ are the same or different and can be a hydrogen atom or an alkyl radical having 1 to 4 carbon atoms. Examples which may be mentioned are phenol, o-cresol, 2-tert.-butylphenol, 2-isopropylphenol, 2-methyl-6-tert.-butylphenol and 2,6-diisopropylphenol.

The reaction is carried out in the presence of a mercaptan.

The n-alkylmercaptan to be employed in an amount of 5 to 30, preferably 20 to 25% by weight, relative to methyl acetoacetate, is one having 8 to 20, preferably 8 to 14 carbon atoms in the molecule. Examples which may be mentioned are n-octylmercaptan, n-decylmercaptan, n-dodecylmercaptan, n-hexadecylmercaptan and n-octadecylmercaptan.

The condensation reaction is carried out by initially introducing methyl acetoacetate, an excess of the phenol and the mercaptan into a stirring vessel and passing in dry hydrogen chloride with cooling at a temperature of about $-10°$ to $+15°$ C. After about 10 to 24, preferably 12 to 16 hours, the condensation is complete, which is seen in that an exothermic heat effect can no longer be observed.

To facilitate stirring, the batch can be diluted with a polar solvent, such as, for example, anisole or phenetole. This is recommended, in particular, towards the end of the reaction. The reaction is preferably carried out in the absence of a solvent.

If the condensation reaction is complete, dissolved hydrogen chloride and water of reaction formed are first removed while warming to about 100° C. and applying vacuum. The excess phenol is then distilled off in vacuo at a temperature of 100° to 200° C. and a pressure of 5 to 50 mbar together with the mercaptan and any solvent which may have been used.

A transesterification catalyst is then added to the batch and the diol component intended for the final product is introduced.

Transesterification catalysts suitable per se for this purpose are known compounds. However, preferred organometallic compounds are those of the metals of groups IVA and IVB of the periodic table of the elements, of the formula II $$M(OR^3)_4 \quad (II),$$

in which M is titanium, zirconium, hafnium, germanium or tin, preferably titanium, and $R^3$ is an alkyl radical having 1 to 18 C atoms, phenyl or benzyl, preferably n-butyl, and dialkyltin compounds of the formula III $$R_2^4SnO \quad (III),$$

in which $R^4$ is an alkyl radical having 4 to 12 carbon atoms, preferably n-butyl.

The catalyst is employed in an amount of 0.05 to 2 mol-%, relative to the reaction product of the first step.

Suitable diol components are aliphatic, araliphatic, cycloaliphatic or aromatic dialcohols. Examples which may be mentioned are ethanediol, propane-1,2-diol, propane-1,3-diol, butane-1,4-diol, hexane-1,6-diol, decane-1,10-diol, dodecane-1,12-diol, 2,2-dimethylpropane-1,3-diol, quinitol, 1,4-dimethylolcyclohexane, hydroquinone, resorcinol and dihydroxynaphthalene. Ethanediol and butane-1,4-diol are preferred.

The alcohol is employed in an amount of 10 to 50 mol-%, relative to the reaction product of the first step.

The reaction is carried out at a temperature of 120° to 240° C., preferably 140° to 200° C., at a pressure of 2 to 300 mbar for 2 to 16 hours. To facilitate stirring, a solvent may be present. However, the reaction is preferably carried out in the absence of a solvent. After the reaction, all the distillable components are removed by vacuum distillation. This distillation is carried out at a pressure of 0.2 to 8 mbar and at a temperature of 220° to 280° C.

The reaction is expediently carried out in a short-time distillation apparatus, for example in a thin layer evaporator, falling-film evaporator or filmtruder.

For most application purposes, the bis[3,3-bis(4-hydroxyalkylphenyl)butanoic acid]diol ester thus obtained has a sufficient purity. If necessary, however, the product can be recrystallized from a solvent, for example toluene, to remove the catalyst residues.

The process according to the invention has the advantage that only a single acetoacetic ester is employed as a starting material in order to prepare various bis[3,3-bis(4-hydroxyalkylphenyl)butanoic acid]diol esters. As a result, the cost of the entire process is reduced. As a rule, the final product is obtained as a melt which can be directly processed further to give powders or flakes. A solvent is only necessary in the second step in exceptional cases.

The following example is intended to illustrate the invention.

EXAMPLE 348 g (2.32 mol) of o-tert.-butylphenol
46.4 g (0.40 mol) of methyl acetoacetate and
16.2 g (0.08 mol) of n-dodecylmercaptan, relative to methyl acetoacetate, were added to a 1 l three-necked flask fitted with a stirrer, gas inlet tube and gas outlet, after which a total of 9.0 g of dry HCl gas was passed into the batch, which was kept at a temperature of 5° to 10° C. After stirring at 5° to 10° C. for 12 hours, the dissolved HCl gas was first distilled off in a water jet vacuum, then the water of reaction formed was distilled off while slowly increasing the bath temperature and finally the excess o-tert.-butylphenol (b.p. 110° C. at 9 mbar) and the dodecylmercaptan (b.p. 133° C. at 9 mbar) were distilled off at an oil bath temperature of 180° C.

0.5 g (0.002 mol) of dibutyltin oxide and 11.2 g (0.18 mol) of ethanediol were added to the methyl 3,3-bis(3-t-butyl-4-hydroxyphenyl)butanoate obtained and the batch was heated to 180° C. under nitrogen and with stirring for 2 hours. The methanol formed distilled off during the course of this. The pressure was then reduced to 20 mbar in the course of 1 hour and the batch was stirred at this pressure for a further 4 hours. The melt was then transferred to a thin layer evaporator and distilled at a temperature of 240° C. and a pressure of 1 mbar. The unreacted methyl 3,3-bis(3-t-butyl-4-hydroxyphenyl)butanoate collected in the receiver can be used again as starting material. The bis[3,3-bis(3-t-butyl-4-hydroxyphenyl)butanoic acid]ethanediol ester melt which remained was cooled under nitrogen and then comminuted.

Yield 135 g (0.17 mol), corresponds to 94% of theory, relative to ethanediol, or 85% of theory, relative to methyl acetoacetate employed. M.p. 98° to 110° C.

We claim:

1. A process for the preparation of a bis[3,3-bis(4-hydroxyalkylphenyl)butanoic acid]diol ester by reaction of an acetoacetic ester with a phenol in the presence of gaseous hydrogen chloride and a $C_8$-$C_{20}$-n-alkylmercaptan, which comprises first reacting methyl acetoacetate with a phenol of the formula I

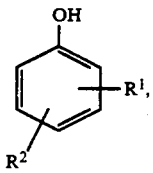

in which $R^1$ and $R^2$ are identical or different and are a hydrogen atom or an alkyl radical having 1 to 4 carbon atoms, at a temperature of $-10°$ to $+15°$ C. in the presence of 5 to 30% by weight, relative to the ester, of an n-alkylmercaptan having 8 to 20 carbon atoms and converting the resulting methyl 3,3-bis(4-hydroxyalkylphenyl)butanoate by transesterification with a diol in the presence of 0.05 to 2 mol-%, relative to the ester, of an organometallic compound of the formula II $$M(OR^3)_4 \quad (II),$$

in which $R^3$ is an alkyl radical having 1 to 18 carbon atoms, phenyl or benzyl and M is a metal of the groups IVA and IVB of the periodic table, or a dialkyltin compound of the formula III $$R_2^4SnO \quad (III),$$

in which $R^4$ is an alkyl radical having 4 to 12 carbon atoms, at a temperature of 120° to 240° C. and a pressure of 2 to 300 mbar into the bis[3,3-bis(4-hydroxyalkylphenyl)butanoic acid]diol ester, which is freed from all distillable components by distillation at a temperature of 220° to 280° C. and a pressure of 0.2 to 8 mbar.

2. The process as claimed in claim 1, wherein o-tert.-butylphenol is employed as the phenol and ethanediol is employed as the diol.

* * * * *